United States Patent

Crookham et al.

[11] Patent Number: 5,952,552
[45] Date of Patent: Sep. 14, 1999

[54] INBRED SWEET CORN LINE CRAUGSH2W-89

[75] Inventors: George W. Crookham; Bruce W. Hobdey, both of Caldwell, Id.; George E. Oswald, Hall, N.Y.

[73] Assignee: Crookham Company, Caldwell, Id.

[21] Appl. No.: 09/084,998

[22] Filed: May 28, 1998

[51] Int. Cl.[6] ................. A01H 5/00; A01H 4/00; C12N 5/04
[52] U.S. Cl. ............. 800/320.1; 800/298; 800/275; 800/271; 435/412; 435/424; 435/430; 435/430.1
[58] Field of Search ................. 800/320.1, 298, 800/875, 271, 363, 274; 435/412, 424, 430, 430.1

[56] References Cited

PUBLICATIONS

Phillips et al. "Cell/tissue Culture and in vitro manipulation" Corn & Corn Improvement, ed SPrague et al. p. 358, 1988.

*Primary Examiner*—Gary Benzion
*Attorney, Agent, or Firm*—Rothwell, Figg, Ernst & Kurz

[57] ABSTRACT

An inbred sweet corn line, designated CRAUGSH2W-89, is disclosed. The invention relates to the seeds of inbred corn line CRAUGSH2W-89, to the plants of inbred corn line CRAUGSH2W-89 and to methods for producing a corn plant produced by crossing the inbred line CRAUGSH2W-89 with itself or another corn line. The invention further relates to hybrid corn seeds and plants produced by crossing the inbred line CRAUGSH2W-89 with another corn line.

13 Claims, No Drawings

INBRED SWEET CORN LINE CRAUGSH2W-89

BACKGROUND OF THE INVENTION

The present invention relates to a new and distinctive sweet corn inbred line, designated CRAUGSH2W-89. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germ-plasm. These important traits may include higher yield, resistance to diseases and insects, better stalks and roots, improved flavor, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s). The best lines are candidates for new commercial cultivars; those elite in traits are used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior sweet corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new sweet corn inbred line.

The development of commercial sweet corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complimentary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parents is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Sweet corn is an important and valuable vegetable crop. Thus, a continuing goal of plant breeders is to develop stable, high yielding sweet corn hybrids that are agronomically sound. The reasons for this goal are obviously to maximize the amount of grain produced on the land used and to supply food for humans. To accomplish this goal, the sweet corn breeder must select and develop sweet corn plants that have the traits that result in superior parental lines for producing hybrids.

SUMMARY OF THE INVENTION

According to the invention, there is provided a novel inbred sweet corn line, designated CRAUGSH2W-89. This invention thus relates to the seeds of inbred sweet corn line CRAUGSH2W-89, to the plants of inbred CRAUGSH2W-89 and to methods for producing a sweet corn plant produced by crossing the inbred line CRAUGSH2W-89 with itself or another corn line. This invention further relates to hybrid sweet corn seeds and plants produced by crossing the inbred line CRAUGSH2W-89 with another corn line.

DEFINITIONS

In the description and tables which follow, a number of terms are used. In order to provide a clear and consistent understanding of the specification and claims, including the scope to be given such terms, the following definitions are provided:

TASSEL. As used herein, the term "Tassel" means the number of days from planting until the hybrid has 50% of the tassels shedding pollen.

SILK. As used herein, the term "Silk" means the number of days from planting until the hybrid has 50% of the silks emerged from the husk.

STALK QUALITY. As used herein, the term "Stalk Quality" means the quality of the plant stalk, and is scored 1 to 5, with 1 being very poor and 5 being excellent.

SHANK LENGTH. As used herein, the term "Shank Length" means the length of the shank measured in inches.

HUSK COLOR. As used herein, the term "Husk Color" means the color of the fresh husk and is scored from 1 to 5.

HUSK PROTECTION. As used herein, the term "Husk Protection (HUSP)" means the husk length and tip coverage, and is scored 1 to 5, with 1 having protruding ears and 5 being very long and tight.

SIZE OF SNAP. As used herein, the term "Size of Snap" means the size of snapped ears. The size is measured by using the diameter at the midpoint of the snapped ear.

SILK COLOR. As used herein, the term "Silk Color" means the color of the silk and is scored 1 to 5.

CORN. As used herein, the term "Corn" means field corn, sweet corn, popcorn, and/or all species under *Zea mays*.

BLANKING. As used herein, the term "Blanking" means how well the tip of the ear is filled out with kernels.

ROW. As used herein, the term "Row" means the number of rows that are present on the ear.

TYPE OF ROWING. As used herein, the term "Type of Rowing" means how straight the rows are on the ear of corn and is scored 1 to 5, with 5 being best.

EAR SHAPE. As used herein, the term "Ear Shape" means how cylindrical or how much of a taper the ear has, and is scored 1 to 5, with 1 being extreme taper and 5 being very cylindrical from butt to tip.

EAR LENGTH. As used herein, the term "Ear Length" means the length of the ear measured in inches.

EAR DIAMETER. As used herein, the term "Diameter (DIA)" means the diameter of the ear measured in inches.

KERNEL DEPTH. As used herein, the term "Kernel Depth" means the depth of a kernel measured in millimeters.

KERNEL WIDTH. As used herein, the term "Kernel Width" means the width of a kernel measured in millimeters.

PERICARP. As used herein, the term "Pericarp (PERI)" means the pericarp of the kernel, and is scored 1 to 5, with 1 being very tough and 5 being very tender.

FLAVOR. As used herein, the term "Flavor (FLAV)" means the flavor of the corn, and is scored 1 to 5, with 1 being gritty starch and 5 being sweet and flavorful.

TEXTURE. As used herein, the term "Texture (TEXT)" means the texture of the kernel, and is scored 1 to 5, with 1 being very starchy and 5 being very creamy consistency.

MATURITY. As used herein, the term "Maturity (MAT)" means the number of days from planting until eating prime, i.e., when the kernels are at approximately 80%–90% moisture.

PLANT HEIGHT. As used herein, the term "Plant Height (PL HT)" means the plant height measured in inches, from the ground to the tip of the tassel.

TILLER HEIGHT. As used herein, the term "Tiller Height" means the height of the tiller as measured in inches.

EAR HEIGHT. As used herein, the term "Ear Height (EA HT)" means the height of the first ear as measured in inches from the ground to the shank attachment of the First Ear on the plant.

EAR YIELD PER PLANT. As used herein, the term "Ear Yield Per" means the average number of mature ears per plant.

NUMBER OF TILLERS. As used herein, the term "Number of Tillers" means the average number of tillers per plant.

DETAILED DESCRIPTION OF THE INVENTION

Inbred sweet corn line CRAUGSH2W-89 is a white sweet corn with superior characteristics, and provides an excellent parental line in crosses for producing first generation ($F_1$) hybrid sweet corn.

CRAUGSH2W-89 is a sweet corn inbred line developed from the single cross of [W232×SLK(Incredible×CNS725)] by selfing and using the pedigree system of plant breeding. Yield, eating quality, plant habitat, disease tolerance, maturity, emergence and vigor, ear shape, and produceability, were the criteria used to determine the rows from which ears were selected.

Inbred sweet corn line CRAUGSH2W-89 has the following morphologic and other characteristics (based primarily on data collected at Caldwell, Id.).

VARIETY DESCRIPTION INFORMATION
1. TYPE: Inbred
2. REGION WHERE DEVELOPED: Caldwell, Id., and Hall, N.Y.
3. MATURITY:

|  | Days |
| --- | --- |
| From emergence to 50% of plants in tassel: | 71 |
| From emergence to 50% of plants in silk: | 70 |

4. PLANT:
   Plant Height (to tassel tip): 44.8 inches
   Ear Height (to base of top ear): 11 inches
   Average number of Tillers: 1
   Erectness of Tillers: Erect
   Average Number of Ears per Stalk: 1.5
5. TASSEL:
   Pollen Shed (Rate on scale from 0=male sterile to 9=heavy shed): 6
   Anther Color: Light green
   Glume Color: Yellow
6a. EAR: (Unhusked Data)
   Silk Color: Green or green cast
   Fresh Husk Color: Good, dark green
   Position of Ear: First Ear Clockwise as at 2:00 o'clock
   Husk Tightness (Rate on scale from 1=very loose to 9=very tight): 7
   Husk Extension: Average, 1–2" beyond ear tip
6b. EAR: (Husked Ear Data)
   Ear Length: 5.8 inches
   Ear Diameter at mid-point: 1.9 inches
   Number of Kernel Rows: 16
   Kernel Rows: Distinct
   Ear Shape: Moderate taper from butt to tip, generally cylindrical
7. KERNEL: (Dried)
   Endosperm Type: Su1Su1sh2sh2
   Weight per 100 kernels (unsized sample): 0.5 ounces
8. AGRONOMIC TRAITS:
   Plant uniformity: fair
   Stack quality: excellent
9. SHANK LENGTH:
   Length of Shank: short, 1" or less
10. SIZE OF SNAP:
    Size of snapped ears (diameter at midpoint): 2.1
11. BLANKING:
    Blanking (Tip Fill): Generally good fill
12. EAR UNIFORMITY:
    Ear Uniformity: Fair Uniformity
13. PERICARP:
    Pericarp: Very Tender
14. FLAVOR:
    Flavor: Excellent Flavor
15. TEXTURE:
    Texture: Good Smooth Consistency.

This invention is also directed to methods for producing a sweet corn plant by crossing a first parent sweet corn plant with a second parent sweet corn plant, wherein the first or second sweet corn plant is the inbred sweet corn plant from the line. Further, both first and second parent sweet corn plants may be from the inbred line. Therefore, any methods using the inbred sweet corn line CRAUGSH2W-89 are part of this invention: selfing, backcrosses, hybrid breeding, and crosses to populations. Any plants produced using inbred sweet corn line CRAUGSH2W-89 as a parent are within the scope of this invention. Advantageously, the inbred sweet corn line is used in crosses with other corn varieties to produce first generation ($F_1$) sweet corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants, such as pollen, flowers, kernels, ears, cobs, leaves, husks, stalks, and the like.

Tissue culture of corn is described in European Patent Application, Publication No. 160,390, incorporated herein by reference. Corn tissue culture procedures are also described in Green and Rhodes, "Plant Regeneration in Tissue Culture of Maize", *Maize for Biological Research* (Plant Molecular Biology Association, Charlottesville, Va. 1982), at 367–372. Thus, another aspect of this invention is to provide for cells which upon growth and differentiation produce the inbred line CRAUGSH2W-89.

CRAUGSH2W-89 is most similar to CrW232, however, there are numerous differences including the tassel color. The tassel color of CRAUGSH2W-89 is yellow while the tassel color of CrW232 is purplish. In addition, the genotype for CRAUGSH2W-89 is different than the su1su1Sh2Sh2 genotype for CrW232. Furthermore, CRAUGSH2W-89 is an augmented shrunken inbred while CrW232 is a sugar enhanced inbred. CrW232 also has increased anthrocyanin while CRAUGSH2W-89 has none. The long, tight, husk protection for CRAUGSH2W-89 is 1½" while the long, tight husk protection for CrW232 is 3".

CRAUGSH2W-89 has a tender pericarp that stays tender longer than standard shrunken 2 inbreds. The kernels in CRAUGSH2W-89 hold texture over time and also have more qualitative sugar, are creamier and have a long-lasting flavor compared to the traditional shrunken inbreds. In addition to improved pericarp, flavor and texture, the CRAUGSH2W-89 kernels create less tugor pressure after prime stage for eating and do not swell, thus they retain a more aesthetic appearance. All of these improved features give CRAUGSH2W-89 an extended shelf life. Thus, CRAUGSH2W-89 has many advantages for both industries and individual consumers.

The inbred has shown uniformity and stability for all traits. It has been self-pollinated and ear-rowed a sufficient number of generations, with careful attention to uniformity of plant type to ensure homozygosity and phenotypic stability.

TABLES

In the tables that follow, the traits and characteristics of inbred sweet corn line CRAUGSH2W-89 are given in hybrid combination along with data on commercial check hybrids. The first four hybrids listed in each table are the hybrids containing CRAUGSH2W-89 as one parent. SS JUBILEE, CHALLENGER, JUBILEE and CNS710 are commercial check hybrids. Information for the hybrids includes the following traits:

In the Tables, Column 1 lists the Hybrid.

Column 2 shows the average HUSK PROTECTION (HUSP), and is recorded by using a score of 1–5, defined as follows:

| | |
|---|---|
| Very Long & Tight 3" or More Beyond Ear Tip | 5 |
| Long and Tight 2–3" Beyond Ear Tip | 4 |
| Average, 1–2" Beyond Ear Tip | 3 |
| Just Adequate, Up to 1" Coverage | 2 |
| Ears Protrude | 1 |

Column 3 has the average ROW number, which is the number of rows that are present on the ear.

Column 4 has the average EAR DIAMETER (DIA), which shows the diameter of the ear measured in inches.

Column 5 has the average PERICARP (PERI), and presents an average based on a scale of 1 to 5, defined as follows:

| | |
|---|---|
| Very Tender | 5 |
| Tender | 4 |
| Average | 3 |
| Slightly Tough | 2 |
| Tough | 1 |

Column 6 has the average FLAVOR (FLAV), resulting from a score of 1 to 5, defined as follows:

| | |
|---|---|
| Sweet & Flavorful | 5 |
| Good Flavor | 4 |
| Average Flavor | 3 |
| Flat or Starchy | 2 |
| Objectionable or Gritty Starch | 1 |

Column 7 has the average TEXTURE (TEXT), resulting from a score of 1 to 5, defined as follows:

| | |
|---|---|
| Very Creamy Consistency | 5 |
| Good Smooth Consistency | 4 |
| Smooth to Watery Consistency | 3 |
| Watery to Starchy Consistency | 2 |
| Very Starchy | 1 |

Column 8 has MATURITY (MAT), and is the average number of days from planting until eating prime.

Column 9 has PLANT HEIGHT (PLHT), and is the average height of the plant, measured in inches, from the ground to the tip of the tassel.

Column 10 has EAR HEIGHT (EAHT), and is the average height of the ear as measured in inches from the ground to the shank attachment of the first ear on the plant.

TABLE 1

1997 COMPARISONS
CALDWELL, IDAHO

| Hybrid | HUSP | ROW | DIA | PERI | FLAV | TEXT | MAT | PLHT | EAHT |
|---|---|---|---|---|---|---|---|---|---|
| CRAUGSH2W-89 × CRSH2-58 | 4 | 16 | 2.0 | 4 | 5 | 3 | 90 | 74 | 29 |
| CRAUGSH2W-89 × CRSH2-79 | 4 | 20 | 2.2 | 3 | 5 | 4 | 85 | 78 | 28 |
| CRAUGSH2W-89 × CR913CE | 1 | 16 | 2.0 | 4 | 4 | 4 | 82 | 64 | 20 |
| CRAUGSH2W-89 × TER/SLK | 2 | 20 | 2.0 | 5 | 5 | 5 | 89 | 69 | 23 |
| SS JUBILEE | 1 | 16 | 1.9 | 3 | 4 | 4 | 90 | 84 | 31 |
| CHALLENGER | 3 | 18 | 2.1 | 3 | 3 | 3 | 87 | 85 | 27 |
| JUBILEE | 1 | 16 | 1.9 | 3 | 3 | 3 | 86 | 81 | 18 |
| CNS710 | 2 | 18 | 2.0 | 3 | 3 | 3 | 84 | 82 | 27 |

TABLE 2

1997 COMPARISONS
DEFOREST, WISCONSIN

| Hybrid | HUSP | ROW | DIA | PERI | FLAV | TEXT | MAT | PLHT | EAHT |
|---|---|---|---|---|---|---|---|---|---|
| CRAUGSH2W-89 × CRSH2-58 | 2 | 16 | 1.8 | 4 | 4 | 3 | 84 | 84 | 30 |
| CRAUGSH2W-89 × CRSH2-79 | 2 | 20 | 2.0 | 4 | 4 | 3 | 84 | 78 | 24 |
| CRAUGSH2W-89 × CR913CE | 2 | 14 | 2.0 | 3 | 4 | 3 | 77 | 78 | 24 |
| CRAUGSH2W-89 × TER/SLK | 2 | 20 | 1.9 | 5 | 5 | 5 | 84 | 66 | 24 |
| SS JUBILEE | 2 | 16 | 1.9 | 4 | 4 | 3 | 86 | 96 | 30 |
| CHALLENGER | 2 | 16 | 1.9 | 3 | 3 | 3 | 82 | 90 | 30 |
| JUBILEE | 2 | 18 | 1.9 | 3 | 3 | 3 | 81 | 96 | 30 |
| CNS710 | 2 | 18 | 1.9 | 3 | 3 | 3 | 81 | 90 | 30 |

TABLE 3

1997 COMPARISONS
HALL, NEW YORK

| Hybrid | HUSP | ROW | DIA | PERI | FLAV | TEXT | MAT | PLHT | EAHT |
|---|---|---|---|---|---|---|---|---|---|
| CRAUGSH2W-89 × CRSH2-58 | 2 | 18 | 1.9 | 3 | 4 | 4 | 84 | 74 | 19 |
| CRAUGSH2W-89 × CRSH2-79 | 2 | 18 | 2.0 | 3 | 4 | 4 | 83 | 67 | 18 |
| CRAUGSH2W-89 × CR913CE | 2 | 14 | 1.9 | 3 | 4 | 3 | 78 | 61 | 14 |
| 14CRAUGSH2W-89 × TER/SLK | — | — | — | 5 | 5 | 5 | 82 | 61 | 15 |
| SS JUBILEE | 1 | 16 | 1.8 | 3 | 4 | 3 | 85 | 69 | 21 |
| CHALLENGER | 2 | 18 | 1.8 | 3 | 4 | 3 | 84 | 67 | 20 |
| JUBILEE | 2 | 16 | 1.8 | 3 | 4 | 3 | 85 | 78 | 26 |
| CNS710 | 2 | 16 | 2.0 | 3 | 4 | 3 | 81 | 65 | 22 |

TABLE 4

1997 OVERALL COMPARISONS

| Hybrid | HUSP | ROW | DIA | PERI | FLAV | TEXT | MAT | PLHT | EAHT |
|---|---|---|---|---|---|---|---|---|---|
| CRAUGSH2W-89 × CRSH2-58 | 2.6 | 16.6 | 1.9 | 4.1 | 4.8 | 3.8 | 86 | 77.3 | 26 |
| CRAUGSH2W-89 × CRSH2-79 | 2.6 | 19.3 | 2.0 | 3.8 | 4.8 | 4.1 | 84.0 | 74.3 | 23.3 |
| CRAUGSH2W-89 × CR91X6 | 1.6 | 14.6 | 1.9 | 3.8 | 4.5 | 3.8 | 79.0 | 67.6 | 19.3 |
| CRAUGSH2W-89 × TER/SLK | 2.0 | 20 | 2.0 | 5.0 | 5.0 | 5.0 | 85.0 | 65.3 | 20.6 |
| SS JUBILEE | 1.3 | 16.0 | 1.8 | 3.3 | 4.0 | 3.3 | 87.0 | 83.0 | 27.3 |
| CHALLENGER | 2.3 | 17.3 | 1.9 | 3.0 | 3.3 | 3.0 | 84.3 | 80.6 | 25.6 |
| JUBILEE | 1.6 | 16.6 | 1.8 | 3.0 | 3.3 | 3.0 | 84.0 | 85.0 | 24.6 |
| CNS710 | 2.0 | 17.3 | 1.9 | 3.0 | 3.3 | 3.0 | 82.0 | 79.0 | 26.3 |

DEPOSIT INFORMATION

A deposit of the Crookham Company inbred sweet corn line CRAUGSH2W-89 disclosed above and recited in the appended claims has been made with the American Type Culture Collection (ATCC), 10801 University Boulevard, Manassas, Va. 20110. The date of deposit was Mar. 4, 1999. The deposit of 2,500 seeds were taken from the same deposit maintained by Crookham Company since prior to the filing date of this application. All restrictions upon the deposit have been removed, and the deposit is intended to meet all of the requirements of 37 C.F.R. §1.801–1.809. The ATCC accession number is ATCC 203809. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. Inbred corn seed designated CRAUGSH2W-89 having ATCC accession No. 203809.

2. A corn plant or its parts produced by growing the seed of claim 1.

3. Pollen of the plant of claim 2.

4. An ovule of the plant of claim 2.

5. A corn plant having all of the physiological and morphological characteristics of the corn plant of claim 2.

6. Tissue culture of the plant of claim 2.

7. A corn plant regenerated from the tissue culture of the plant of claim 6, wherein said corn plant is capable of expressing all of the physiological and morphological characteristics of inbred corn line CRAUGSH2W-89.

8. A method for producing a hybrid corn seed comprising crossing a first inbred parent corn plant with a second inbred parent corn plant and harvesting the resultant hybrid corn seed, wherein said first or second parent corn plant is the corn plant of claim 2.

9. A hybrid seed produced by the method of claim 8.

10. A hybrid plant or its parts produced by growing said hybrid corn seed of claim 9.

11. A method for producing a hybrid corn seed comprising crossing an inbred plant according to claim 2 with another, different corn plant and harvesting the resultant hybrid corn seed.

12. A hybrid seed produced by the method of claim 11.

13. A hybrid plant or its parts produced by growing said hybrid corn seed of claim 12.

* * * * *